United States Patent [19]

Lowery et al.

[11] Patent Number: 5,264,087
[45] Date of Patent: Nov. 23, 1993

[54] METHOD FOR REFINING ACETIC ANHYDRIDE BY DISTILLATION

[75] Inventors: H. Ford Lowery; Steven L. Cook; Vicky K. Pinto, all of Kingsport, Tenn.

[73] Assignee: Eastman Kodak Company, Rochester, N.Y.

[21] Appl. No.: 959,956

[22] Filed: Oct. 13, 1992

[51] Int. Cl.$^5$ .......................... B01D 3/14; C07C 53/12
[52] U.S. Cl. .............................. 203/80; 203/DIG. 19; 562/892; 562/898
[58] Field of Search ......................... 203/80, DIG. 19; 562/898, 892

[56] References Cited

U.S. PATENT DOCUMENTS

| | | | |
|---|---|---|---|
| 2,159,146 | 5/1939 | Guinot | 203/60 |
| 2,232,705 | 2/1941 | Hull | 562/892 |
| 2,504,195 | 4/1950 | Hall et al. | 562/898 |
| 2,703,309 | 3/1955 | Painter | 562/892 |
| 4,107,002 | 8/1978 | Eck et al. | 562/898 |
| 4,717,454 | 1/1988 | Erpenbach et al. | 203/DIG. 6 |
| 5,057,192 | 10/1991 | Zoeller et al. | 203/DIG. 19 |

FOREIGN PATENT DOCUMENTS

| | | | |
|---|---|---|---|
| 50-22532 | 7/1975 | Japan | 562/898 |
| 62-246536 | 10/1987 | Japan | 562/898 |

Primary Examiner—Wilbur Bascomb, Jr.
Attorney, Agent, or Firm—J. Frederick Thomsen; William P. Heath, Jr.

[57] ABSTRACT

Disclosed is a continuous method for refining acetic anhydride produced by the reaction of ketene and acetic acid by means of a vacuum distillation system to provide a refined material comprised of at least 99.5 weight percent acetic anhydride, not more than 0.5 weight percent acetic acid and not more than about 90 parts per million (ppm) diketene.

2 Claims, No Drawings

METHOD FOR REFINING ACETIC ANHYDRIDE BY DISTILLATION

This invention pertains to a novel method for refining acetic anhydride produced by the reaction of ketene and acetic acid. More specifically, this invention pertains to a vacuum distillation method for purifying a stream comprised predominantly of acetic anhydride and acetic acid with minor amounts of diketene to obtain a refined material comprised of at least 99.5 weight percent acetic anhydride, not more than 0.5 weight percent acetic acid and not more than 90 parts per million (ppm) diketene.

The manufacture of acetic anhydride from ketene and acetic acid produces a crude product stream comprising about 83 to 87 weight percent acetic anhydride, about 13 to 17 weight percent acetic acid and about 50 to 110 ppm diketene. The crude product stream has been refined by distillation using sub atmospheric pressures to avoid or minimize degradation of the acetic anhydride. For example, the use of pressures of about 200 torr may be utilized to obtain acetic anhydride having a purity sufficient for general acetylation purposes. Such a grade of acetic anhydride typically comprises at least 99.5 weight percent acetic anhydride, not more than 0.5 weight percent acetic acid and not more than about 90 parts per million (ppm) diketene and has a Hunter color of not more than 10.

We have discovered that acetic anhydride of the above described grade can be produced continuously using two distillation columns and a particular combination of pressures and temperatures. The method of the present invention therefore provides a continuous mean for obtaining purified acetic anhydride comprising at least 99.5 weight percent acetic anhydride, not more than 0.5 weight percent acetic acid and not more than about 90 ppm diketene and having a Hunter color of not more than 10 by the steps comprising:

(1) feeding a mixture comprising about 83 to 87 weight percent acetic anhydride, about 13 to 17 weight percent acetic acid and about 50 to 110 ppm diketene to the mid section of an acid removal distillation column in which (i) a column base temperature of about 114° to 127° C., (ii) a column head temperature of about 87° to 105° C., and (iii) a column top pressure of about 225 to 350 torr are maintained;

(2) removing from the head of the acid removal distillation column a first stream comprised of about 20 to 30 weight percent acetic anhydride, about 70 to 80 weight percent acetic acid and about 10 to 40 ppm diketene;

(3) removing a second stream from the base of the acid removal distillation column and feeding the second stream to the base of a color column in which (i) a column base temperature of about 101° to 105° C., (ii) a column head temperature of about 97° to 100° C., and (iii) a column top pressure of about 225 to 350 torr are maintained; and (4) removing from the mid section of the color column a stream comprising the purified acetic anhydride.

The acid removal distillation column preferably is operated at (i) a column base temperature of about 125° to 127° C., (ii) a column head temperature of about 103° to 105° C., and (iii) a column top pressure of about 330 to 350 torr, and the color column preferably is operated at (i) a column base temperature of about 101° to 105° C., (ii) a column head temperature of about 97° to 100° C., and (iii) a column top pressure of about 330 to 350 torr.

In the following description illustrating the operation of the process, the parts given are by volume. The acetic anhydride/acetic acid mixture having the composition described above is fed continuously to the mid-section of the acid removal column at a rate of 90 to 100 parts per minute. The exact feed point can vary depending, for example, on the particular design of the column and/or the column internals used. The mid-section feed point normally will be at a point which is from 50 to 80% of the distance from the bottom to the top of the acid removal column. In the specific apparatus used in the present invention the feed point is located 77% from the base of the column. The acid removal column is equipped with conventional trays and/or packing material to achieve the desired degree of anhydride/acid separation. We have found that beds of metal slotted ring packing material, both above and below the feed point, provide good separation.

The base of the acid removal column is maintained at a temperature of about 125° to 127° C. by means of a heat source. For example, a portion of the column underflow stream may be recycled through a heat exchanger (reboiler) and returned to the base of the column. The sub atmospheric pressure specified above is measured at the top or head of the acid removal column. The pressure at the base of the column generally is about 80 to 90 torr more than that existing at the top. A mixture comprising about 20 to 30 weight percent acetic anhydride and about 70 to 80 weight percent acetic acid is removed continuously from the top of the column.

The stream removed from the base of the acid removal column is unacceptably dark in color due to the presence therein of colored materials such as carbonaceous compounds and other decomposition products resulting from the acetic anhydride manufacturing process and/or the reboiler employed in conjunction with the first distillation. The highly colored material removed from the base of the acid removal column is pumped to the base of a color distillation column in which (i) a column base temperature of about 101° to 105° C., (ii) a column head temperature of about 97° to 100° C., and (iii) a column top pressure of about 330 to 350 torr are maintained. The color distillation column is equipped with trays and/or packing material and a heat source in a manner analogous to the acid removal column.

The purified acetic anhydride having the composition set forth above is removed from the mid-section of the color distillation column at a rate of 80 to 90 parts per minute. The removal of the colored material is accomplished by continuously removing from the base of the color distillation column a stream comprised mainly of acetic anhydride in addition to the color-causing material at a rate of 1 to 5 parts per minute. A third stream comprising about 89 to 98 weight percent acetic anhydride, 2 to 11 weight percent acetic acid and 100 to 300 ppm diketene is removed from the top of the color distillation column at a rate of 1 to 3 parts per minute.

The invention has been described in detail with particular reference to preferred embodiments thereof, but it will be understood that variations and modifications can be effected within the spirit and scope of the invention.

We claim:

1. Continuous process for obtaining purified acetic anhydride comprising at least 99.5 weight percent acetic anhydride, not more than 0.5 weight percent acetic acid and not more than about 90 ppm diketene and having a Hunter color of not more than 10 by the steps comprising:
   (1) continuously feeding a mixture comprising about 83 to 87 weight percent acetic anhydride, about 13 to 17 weight percent acetic acid and about 50 to 110 ppm diketene to the mid-section of an acid removal distillation column in which (i) a column base temperature of about 114° to 127° C., (ii) a column head temperature of about 87° to 105° C., and (iii) a column top pressure of about 225 to 350 torr are maintained;
   (2) continuously removing from the head of the acid removal distillation column a first stream comprised of about 20 to 30 weight percent acetic anhydride, about 70 to 80 weight percent acetic acid and about 10 to 40 ppm diketene;
   (3) continuously removing a second stream from the base of the acid removal distillation column and feeding the second stream to the base of a color distillation column in which (i) a column base temperature of about 101° to 105° C., (ii) a column head temperature of about 97° to 100° C., and (iii) a column top pressure of about 225 to 350 torr are maintained;
   (4) continuously removing from the mid-section of the color distillation column a stream comprising the purified acetic anhydride;
   (5) continuously removing from the base of the color distillation column a stream comprised of acetic anhydride and color-causing materials; and
   (6) continuously removing from the top of the color distillation column a stream comprised of about 89 to 98 weight percent acetic anhydride, about 2 to 11 weight percent acetic acid and 100 to 300 ppm diketene.

2. Continuous process for obtaining purified acetic anhydride comprising at least 99.5 weight percent acetic anhydride, not more than 0.5 weight percent acetic acid and not more than about 90 ppm diketene and having a Hunter color of not more than 10 by the steps comprising:
   (1) continuously feeding a mixture comprising about 83 to 87 weight percent acetic anhydride, about 13 to 17 weight percent acetic acid and about 50 to 110 ppm diketene to the mid-section of an acid removal distillation column in which (i) a column base temperature of about 125° to 127° C., (ii) a column head temperature of about 103° to 105° C., and (iii) a column top pressure of about 330 to 350 torr are maintained;
   (2) continuously removing from the head of the acid removal distillation column a first stream comprised of about 20 to 30 weight percent acetic anhydride, about 70 to 80 weight percent acetic acid and about 10 to 40 ppm diketene;
   (3) continuously removing a second stream from the base of the acid removal distillation column and feeding the second stream to the base of a color distillation column in which (i) a column base temperature of about 101° to 105° C., (ii) a column head temperature of about 97° to 100° C., and (iii) a column top pressure of about 330 to 350 torr are maintained;
   (4) continuously removing from the mid-section of the color distillation column a stream comprising the purified acetic anhydride;
   (5) continuously removing from the base of the color distillation column a stream comprised of acetic anhydride and color-causing materials; and
   (6) continuously removing from the top of the color distillation column a stream comprised of about 89 to 98 weight percent acetic anhydride, about 2 to 11 weight percent acetic acid and 100 to 300 ppm diketene.

* * * * *